United States Patent
Cattaneo et al.

(10) Patent No.: US 8,765,190 B2
(45) Date of Patent: Jul. 1, 2014

(54) INJECTABLE STERILE PHARMACEUTICAL COMPOSITION WITH PIPERACILLIN SODIUM AND TAZOBACTAM SODIUM AS ACTIVE PRINCIPLES

(75) Inventors: Angelo Giovanni Cattaneo, Monte Marenzo (IT); Leonardo Marsili, Brescia (IT)

(73) Assignee: ACS Dobfar S.p.A., Tribiano (IT)

( * ) Notice: Subject to any disclaimer, the term of this patent is extended or adjusted under 35 U.S.C. 154(b) by 1714 days.

(21) Appl. No.: 11/951,589

(22) Filed: Dec. 6, 2007

(65) Prior Publication Data

US 2008/0233196 A1    Sep. 25, 2008

(30) Foreign Application Priority Data

Mar. 22, 2007 (IT) .............................. MI2007A0568

(51) Int. Cl.
*A01N 59/06* (2006.01)
*A61K 33/10* (2006.01)

(52) U.S. Cl.
CPC ..................................... *A61K 33/10* (2013.01)
USPC ....................................................... 424/686

(58) Field of Classification Search
CPC ..................................................... A61K 33/10
USPC ......................................................... 424/686
See application file for complete search history.

(56) References Cited

U.S. PATENT DOCUMENTS

| 4,344,955 A * | 8/1982 | Niemers et al. ............... 514/194 |
| 2005/0171077 A1 | 8/2005 | Ruppen et al. |
| 2007/0054889 A1 | 3/2007 | Zenoni et al. |

FOREIGN PATENT DOCUMENTS

| EP | 1 759 697 | 3/2007 |
| WO | 2004/098643 | 11/2004 |
| WO | 2006/044600 | 4/2006 |

OTHER PUBLICATIONS

Arzuaga et al (Biomed Chromatogr 19 (2005) 570-578).*
Lauwers et al (Eur. J. Clim. Microbiol. Infect. Dis., vol. 10 (1991) pp. 652-656).*
Pfaller et al (Eur. J. Clim. Microbiol. Infect. Dis., vol. 12 (1993) pp. 200-205).*

* cited by examiner

*Primary Examiner* — Benjamin Packard
(74) *Attorney, Agent, or Firm* — Oblon, Spivak, McClelland, Maier & Neustadt, L.L.P.

(57) ABSTRACT

A sterile pharmaceutical composition having as its active principles piperacillin sodium and tazobactam sodium of substantially the same density, mixed with sodium bicarbonate. The mixture is soluble in water to give injectable reconstituted solutions having high stability with time.

4 Claims, No Drawings

INJECTABLE STERILE PHARMACEUTICAL COMPOSITION WITH PIPERACILLIN SODIUM AND TAZOBACTAM SODIUM AS ACTIVE PRINCIPLES

BACKGROUND OF THE INVENTION

1. Field of the Invention

The present invention relates to a time-stable sterile pharmaceutical composition comprising piperacillin sodium and tazobactam sodium mixed with sodium bicarbonate, this composition being soluble in water to give an injectable sterile solution highly stable with time.

2. Discussion of the Background

EP 1759697A and the corresponding application published under No. 2007/0054889A1 in the name of the present applicants describe the preparation of a stable, sterile homogeneous mixture of piperacillin sodium and tazobactam sodium of substantially the same density, which is soluble in water to give a reconstituted solution with a pH of about 5.6.

During tests carried out after filing EP1759697A it was however observed that the said sterile solution can give rise to a precipitate or to turbidity some minutes after its preparation. This quantitatively very limited precipitate, or possible turbidity, renders the solution unsuitable for clinical use, also in consideration of the fact that administration of the drug by injection does not always immediately follow the preparation of the injectable solution, but several minutes can pass between the solution preparation and its administration to the patient.

SUMMARY OF THE INVENTION

It has now been surprisingly found that if a small quantity of sterile sodium bicarbonate is added to the mixture of tazobactam sodium and piperacillin sodium obtained in accordance with the teachings of EP 1759697A by a process according to which at least one active principle is dissolved in acid form, at a temperature between −10° C. and +25° C., in a solvent consisting of at least one chosen from the group consisting of water, acetone, methanol, ethanol, then salifying the mixture by adding suitable sodium salts chosen from the group consisting of sodium carbonate, sodium 2-ethylhexanoate, sodium acetate, sodium citrate, sodium lactate, sodium methylate, sodium ethylate, sterilely filtering the solution obtained, precipitating the salified mixture by feeding the sterile solution dropwise into at least one organic solvent chosen from the group consisting of isopropyl alcohol, ethyl alcohol, methyl acetate, ethyl acetate, acetone, methylene chloride at a temperature between 0° C. and 50° C., filtering the saline mixture obtained and finally drying it under vacuum at a temperature between 20° C. and 75° C., a solid sterile pharmaceutical composition is obtained which is easily soluble in water to give reconstituted solutions of high stability with time and in which the dissolved piperacillin also remains stable.

In this respect, the sodium bicarbonate presents no problem during its mixing with the active principles, in contrast to other buffer agents which could be considered and which can contain water of crystallization (e.g. sodium citrate) which is potentially damaging to the stability of the dry product.

More specifically, the present invention relates to a stable injectable sterile pharmaceutical composition comprising a mixture of active components consisting of amorphous solid particles of piperacillin sodium and tazobactam sodium in a weight ratio of about 8:1, characterised by also comprising sterile sodium bicarbonate in a quantity between 1.1% and 1.2% on the total weight of said active components, the pharmaceutical composition being soluble in water to give reconstituted solutions of pH between 6.0 and 6.5 having high stability with time.

The preparation process for the aforesaid composition is characterised by adding between 1.1 wt % and 1.2 wt % of sterile sodium bicarbonate to, and carefully mixing it with, a mixture of active components consisting of amorphous solid particles of piperacillin sodium and tazobactam sodium in a weight ratio of about 8:1 obtained in accordance with the teachings of EP1759697A.

DETAILED DESCRIPTION OF THE INVENTION

The characteristics of the composition of the invention and of its preparation process will be more apparent from the ensuing description of two non-limiting examples thereof.

Example 1

0.32 g of sterile sodium bicarbonate are added in a sterile environment to a sterile mixture containing piperacillin sodium and tazobactam sodium (prepared in accordance with EP1759697A) starting from 30 g of acid piperacillin and 3.75 g of acid tazobactam.

The sterile mixture is carefully mixed before effecting the dissolution tests. The pH of the solution obtained by dissolving 1.264 g of mixture in 2 ml of water is 6.1, with no piperacillin degradation occurring.

Example 2

29.3 g of a sterile mixture of piperacillin sodium and tazobactam sodium prepared in accordance with EP1759697A is carefully mixed under sterile conditions with 0.34 g of sterile sodium bicarbonate. The pH of the solution obtained by dissolving 1.265 g of mixture in 2 ml of water is 6.4, with no piperacillin degradation occurring.

The invention claimed is:

1. A composition comprising a mixture of solid particles of piperacillin sodium, solid particles of tazobactam sodium in a weight ratio of about 8:1, and sterile sodium bicarbonate in a quantity of from 1.1% to 1.2% based on the total weight of solid particles of piperacillin sodium and tazobactam sodium, the mixture being soluble in water to give a reconstituted solution with a pH of 6.0 to 6.5 having high stability with time.

2. A preparation process for the composition as claimed in claim 1, wherein between 1.1 wt % and 1.2 wt % of sterile sodium bicarbonate are added to, and are carefully mixed with, a mixture of active components consisting of solid particles of piperacillin sodium and tazobactam sodium in a weight ratio of about 8:1 obtained by dissolving at least one of the active components in acid form, at a temperature of from −10° C. and 25° C., in at least two solvents selected from the group consisting of water, acetone, methanol, isopropylalcohol, and ethanol, salifying the mixture by adding a sodium salt selected from the group consisting of sodium carbonate, sodium 2-ethyl hexanoate, sodium acetate, sodium citrate, sodium lactate, sodium methylate, and sodium ethylate to obtain a salified solution, sterilely filtering the salified solution and precipitating the salified solution by feeding the sterilely filtered salified solution dropwise into at least one organic solvent selected from the group consisting of isopropyl alcohol, ethyl alcohol, methyl acetate, ethyl acetate, acetone, and methylene chloride at a temperature of from 0° C. and 50° C., filtering the resultant mixture, and during the mixture under vacuum at a temperature of from 20° C. to 75° C.

3. A stable injectable sterile pharmaceutical composition comprising solid particles of piperacillin sodium, solid particles of tazobactam sodium, from 1.1 to 1.2% sterile sodium bicarbonate based on the total weight of solid particles of piperacillin sodium and tazobactam sodium, and water, wherein the solid particles of piperacillin sodium and tazobactam sodium are in a weight ratio of about 8:1, wherein the stable injectable sterile pharmaceutical composition has a pH of 6.0 to 6.5.

4. A preparation process for the injectable sterile pharmaceutical composition as claimed in claim 3, the method comprising adding and mixing from 1.1 wt % to 1.2 wt % of sterile sodium bicarbonate to a mixture of solid particles of piperacillin sodium and tazobactam sodium in a weight ratio of about 8:1 obtained by dissolving at least one of the solid particles of piperacillin sodium and tazobactam sodium in acid form, at a temperature of from −10° C. and 25° C., in at least two solvents selected from the group consisting of water, acetone, methanol, isopropylalcohol, and ethanol, salifying the mixture by adding a sodium salt selected from the group consisting of sodium carbonate, sodium 2-ethyl hexanoate, sodium acetate, sodium citrate, sodium lactate, sodium methylate, and sodium ethylate to obtain a salified solution, sterilely filtering the salified solution and precipitating the salified solution by feeding the sterilely filtered salified solution dropwise into at least one organic solvent selected from the group consisting of isopropyl alcohol, ethyl alcohol, methyl acetate, ethyl acetate, acetone, and methylene chloride at a temperature of from 0° C. and 50° C., filtering the resultant mixture, and during the mixture under vacuum at a temperature of from 20° C. to 75° C.

\* \* \* \* \*